United States Patent [19]

Chinn

[11] Patent Number: 5,906,612
[45] Date of Patent: May 25, 1999

[54] CRYOSURGICAL PROBE HAVING INSULATING AND HEATED SHEATHS

[76] Inventor: Douglas O. Chinn, 1336 N. Santa Anita Ave., Arcadia, Calif. 91006

[21] Appl. No.: 08/934,497

[22] Filed: Sep. 19, 1997

[51] Int. Cl.$^6$ .................................................. A61B 17/36
[52] U.S. Cl. ................................ 606/20; 606/21; 606/23
[58] Field of Search ............................................. 606/20–26

[56] References Cited

U.S. PATENT DOCUMENTS

| | | |
|---|---|---|
| 3,911,924 | 10/1975 | Zimmer . |
| 3,948,269 | 4/1976 | Zimmer . |
| 3,971,383 | 7/1976 | Van Gerven . |
| 4,202,336 | 5/1980 | Van Gerven . |
| 5,520,682 | 5/1996 | Baust et al. ............................. 606/24 |
| 5,733,280 | 3/1998 | Avitall ..................................... 606/23 |

*Primary Examiner*—Lee Cohen
*Assistant Examiner*—Roy Gibson
*Attorney, Agent, or Firm*—Morland C. Fischer

[57] ABSTRACT

A cryosurgical probe and method for treating cancer by cryosurgically destroying cancer cells by way of an ice ball formed at the distal end of the cryosurgical probe being located in proximity to the cancerous tissue to be treated. The probe is surrounded by a thermally insulating sheath. By varying the length and thickness of the thermally insulating sheath as well as the length of the unsheathed distal tip of the probe, the size and shape of the ice ball produced by the cryosurgical probe can be controllably tailored to correspond to the size, shape and location of the cancerous tissue so as to localize the cryogenic effect. Alternatively, the size and shape of the ice ball can be controlled by surrounding the cryosurgical probe with a heated sheath having a heating element and a temperature sensor to detect the temperature to which the sheath is heated.

20 Claims, 3 Drawing Sheets

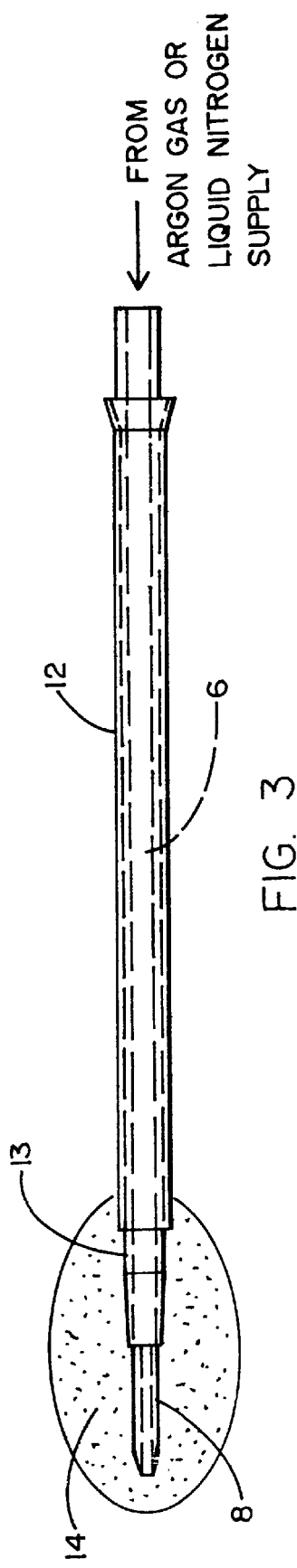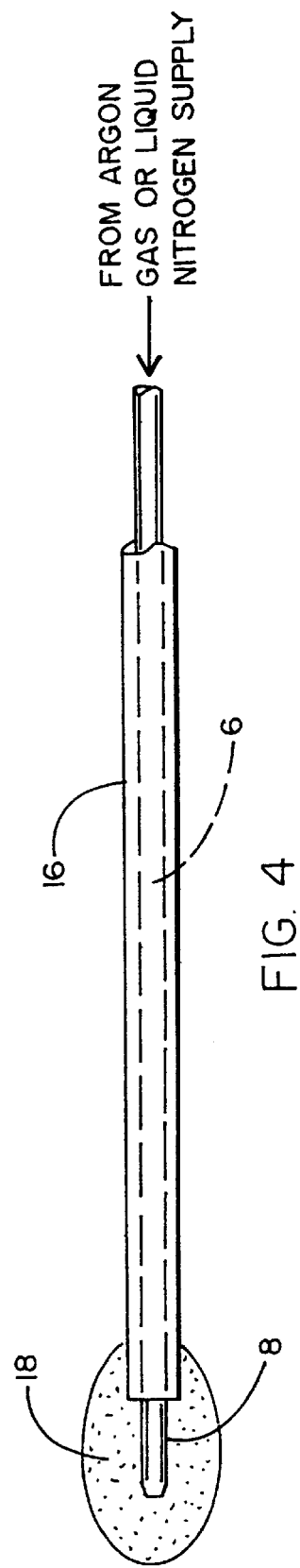

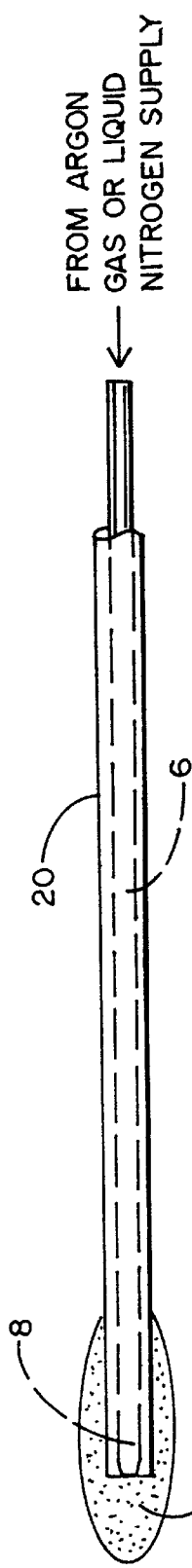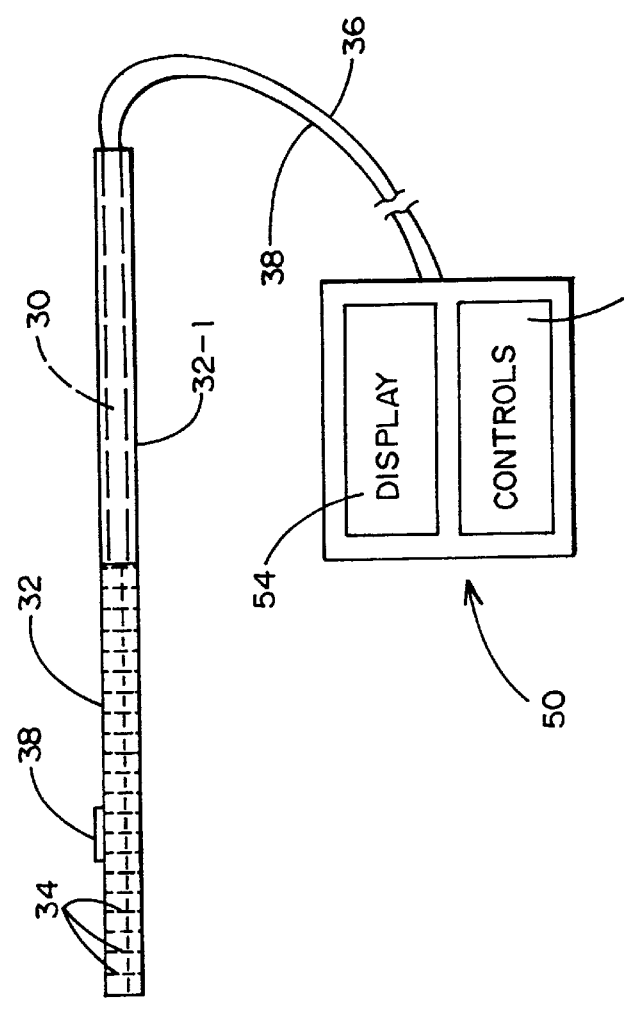

CRYOSURGICAL PROBE HAVING INSULATING AND HEATED SHEATHS

BACKGROUND OF THE INVENTION

1. Field of the Invention

This invention relates to a cryosurgical probe and method for treating cancer by cryosurgically destroying the cancer cells. The probe is surrounded by a thermally insulating and/or heated sheath having particular dimensions so as to produce an ice ball having a corresponding size and shape that are tailored to the size, shape and location of the cancerous tissue.

2. Background Art

Cryosurgical devices have been known for use in destroying cancerous cells in a localized tissue area of a patient undergoing treatment. Early cryosurgical devices used gases or liquid nitrogen to generate extremely low temperatures to kill cancerous cells. The gaseous system typically relied on the Jewel-Thompson principal to produce a cryogenic effect, and the liquid system was based directly upon the thermal characteristics of the liquid nitrogen. Such early devices were used solely for the surface treatment of pathologic lesions but not to penetrate human tissue. These early devices are characterized by relatively low pressure (e.g. about 6 psi) and interchangeable tips to provide a desired result. Consequently, the early cryosurgical devices had limited cryogenic capacity and correspondingly limited application.

More recent cryosurgical devices are either of higher pressure (e.g. about 80 psi) liquid nitrogen systems or high pressure (e.g. 2,800 psi) argon gas systems. Such devices are typically characterized by a closed end probe in which the cryogen circulates to the probe tip. The probe tips are adapted to penetrate the patient's tissue (e.g. the prostate, liver, breast and brain) in which the cancerous cells reside. However, these recent cryosurgical probes cannot be easily modified to accept tip changes without significantly effecting the probe performance. Likewise, the cost to redesign a probe to accept different tips is expensive and often leads to operating characteristics that may not be suitable for all applications (i.e. the cryogenic effect could be severely compromised).

For example, a significant problem that is faced in prostate surgery is that the size and shape of the prostate gland varies from one patient to the next. If the ice ball that is generated by the cryogenic effect is too long, there is the risk that the neighboring sphincter will also be frozen resulting in the possibility of incontinence. If the patient's prostate is cylindrical rather than ellipsoid, the ice ball may not adequately conform to the prostate shape, whereby to introduce a risk of incomplete freezing of the cancerous cells in the prostate gland or freezing beyond the prostate and into the bladder or rectum resulting in the possibility of a urethral-rectal fistula. What is more, the round and/or tear drop shaped ice ball that is usually produced by the conventional cryoprobe does not fit well within the generally tubular seminal vesicle that is attached to the prostate which may lead to an unsuccessful procedure or other complications.

Therefore, what is needed is a cryosurgical probe that is quickly, easily and inexpensively adapted to vary the size and shape of an ice ball during cryosurgery depending upon the location and type of tissue to be treated so as to confine the cryogenic effect to a localized cancerous area and thereby avoid the risks that are associated with conventional cryoprobes.

SUMMARY OF THE INVENTION

An apparatus and method are disclosed in which a conventional cryosurgical probe is surrounded by insulating sheaths of varying dimension so that the same probe can be used to generate different ice balls at the distal probe tip. The size and shape of the ice ball corresponds with the dimensions of the insulating sheath which surrounds the cryosurgical probe. Therefore, the size and shape of the ice ball can be advantageously tailored to the type and location of the cancerous tissue in need of treatment and at which a cryogenic effect is to be produced.

Initially, a standard dilator is surrounded by the insulating sheath. The sheath is preferably manufactured from Teflon, polypropylene, urethane or any suitable biocompatible plastic. The dilator is a hollow tube that is commonly used to stretch the patient's tissue and cut an access channel to the area in which the cancerous cells reside. Once the access channel is established, the dilator is withdrawn from the patient's tissue leaving behind the insulating sheath. Next, a conventional cryosurgical probe is inserted into the access channel and through the insulating sheath so that either some or all of the probe is surrounded by the sheath. The probe is typically coupled to a supply of argon gas or liquid nitrogen so that an ice ball can be formed at the distal tip thereof, whereby to produce a cryogenic effect and thereby kill the cancer cells.

By varying the length and thickness of the insulating sheath surrounding the cryosurgical probe as well as the length of the unsheathed distal tip of the probe, the size and shape of the ice ball can be correspondingly varied to match the size, shape and location of the effected tissue (e.g. the prostate gland). Alternatively, the distal end of the cryosurgical probe is surrounded by a heated sheath having an electrical heating element coupled thereto. By regulating the current being supplied to the heating element, the size and shape of the ice ball can be controllably adjusted depending upon the corresponding temperature to which the sheath is heated. Accordingly, cryosurgery can be more reliably and efficiently performed without the need for a multitude of different probes or probe tips and with the ability to localize the cryogenic effect to the particular area of cancerous tissue.

BRIEF DESCRIPTION OF THE DRAWINGS

FIGS. 2–5 show the cryosurgical probe of FIG. 1 surrounded by insulating sheaths of different dimensions so as to produce ice balls of corresponding sizes and shapes; and FIG. 6 shows an alternate embodiment where the cryosurgical probe is surrounded by a heated sheath to control the size and shape of the ice ball.

DETAILED DESCRIPTION

Figure 1:
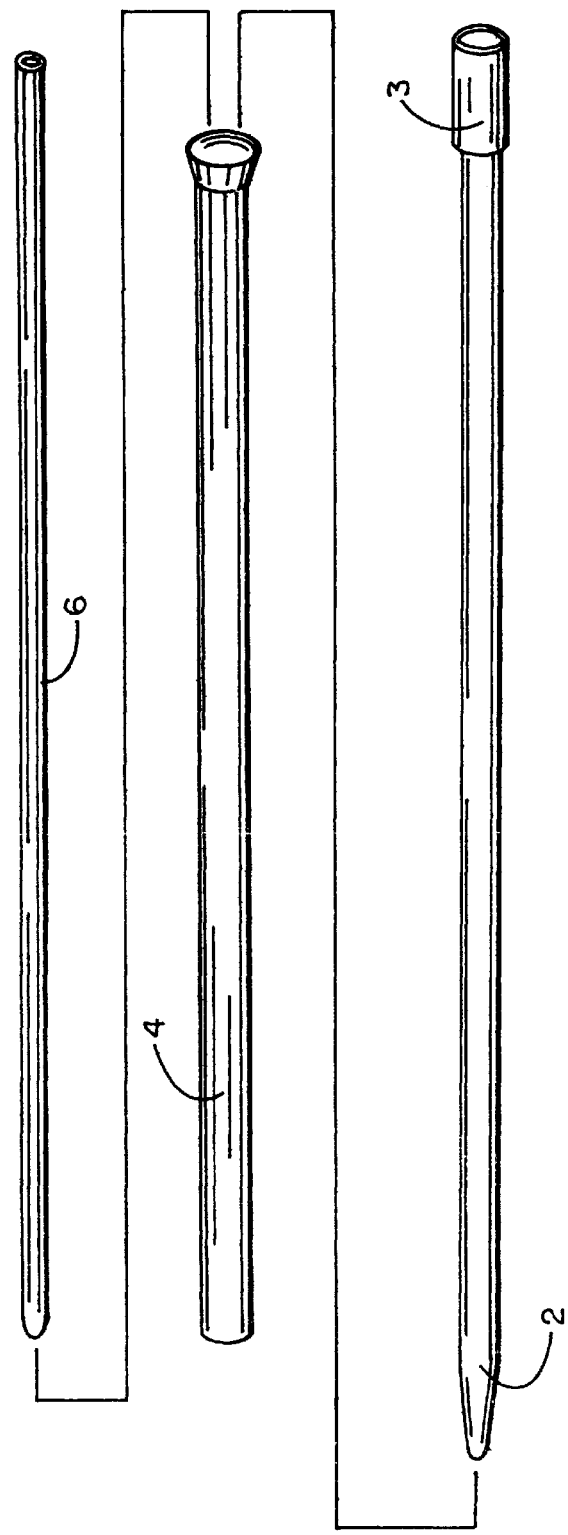
FIG. 1 is an exploded view showing the relationship of the cryosurgical probe for producing an ice ball, the dilator for cutting an access channel for the probe, and the insulating sheath for surrounding the probe.

According to the improvement of the present invention, an apparatus and method are disclosed in which a conventional cryosurgical probe is surrounded by thermally insulating sheaths of varying dimensions so that the same probe can be used to generate ice balls of corresponding size and shape so as to overcome the shortcomings that are associated with conventional cryoprobes. That is to say, the size and shape of an ice ball can be tailored according to the type and location of the cancerous tissue in need of treatment.

By virtue of being able to selectively vary the size and shape of the ice ball depending upon the dimensions of the insulating sheath, the cryogenic effect can be accurately localized, whereby to avoid the risks that less than all of the cancerous cells will be frozen or that non-cancerous tissue will be frozen and possibly damaged. Moreover, it will no longer be necessary to redesign or substitute probes or probe tips for use in treating different patients. By merely surrounding the cryosurgical probe with an inexpensive and disposable insulating sheath, the same cryoprobe can be quickly, easily and reliably adapted for different cryosurgical applications for which different ice balls are required.

In support of my aforementioned discovery, I conducted tests wherein a plurality of conventional surgical probes were fully exposed (i.e. unsheathed) and completely or partially surrounded by respective thermally insulating sheaths having different lengths and thicknesses. I used well known peel away sheaths manufactured from a material sold commercially as Teflon. However, sheaths manufactured from polypropylene, urethane and other suitable biocompatible plastics can also be used. The cryosurgical probes were supported by test fixtures so as to be held both vertically and horizontally.

The sizes and shapes of the resulting ice balls at the distal tips of the cryosurgical probes were recorded for the sheathed and unsheathed cryoprobes. Measurements were made at different times for about 10 minutes. In some cases, a cryoprobe was surrounded by a single sheath thickness and in other cases by a double sheath thickness. In yet other cases, the thickness of the sheath varied along the length of the cryoprobe. During the aforementioned tests, photographs were taken and the overall size and shape of the ice balls were compared. Particular attention was paid to the differences in the inner white ice formation (which has proven to be lethal to cancer cells) and to the outer clear ice formation (which is usually not lethal to cancer cells).

At the conclusion of the tests, it was found that surrounding some or all of a cryosurgical probe with a sheath of thermally insulating material of varying length and wall thickness produces ice balls of varying size and shape and white ice formation depending upon the specific dimensions of the sheath. The foregoing test results are generally illustrated in the drawings described below.

FIG. 1 of the drawings shows a well known dilator 2 having a rigid hollow tube of plastic or stainless steel that is commonly used to stretch the patient's tissue and cut an access channel in the proximity of the tissue area in need of treatment. The dilator 2 has a relatively sharp point so as to be able to cut through the patient's tissue. The method for inserting the dilator 2 into the body cavity and towards the tissue to be treated is well known (e.g. a Seldinger access technique) in cryosurgery. The dilator 2 penetrates the patient's tissue while being surrounded by a peel away insulating sheath 4 of a predetermined size that is adapted to generate the particular ice ball necessary to treat the patient's cancer. In particular, the sheath surrounds and rides with the dilator 2 when the access channel is formed. The dilator 2 has a relatively wide stop or handle 3 located at the end opposite the cutting tip so as to block the insulating sheath 4 from sliding proximally and off the dilator 2 when the dilator penetrates the patient's tissue.

While the maximum length of the insulating sheath 4 will vary depending upon the size and location (e.g. depth) of the cancerous tissue to be treated, it has been found that the minimum length of the insulating sheath 4 should be approximately 15 cm for treating cancerous prostate glands. However, the minimum length of the sheath 4 may change when treating other cancerous tissue.

Once the dilator 2 completes an access channel to the cancerous tissue, it is withdrawn leaving behind the insulating sheath 4. Next, a conventional cryosurgical probe 6 is inserted into the access channel and through the insulating sheath 4. As will be known to those skilled in the art, the cryosurgical probe 6 is typically a cylindrical tube that is adapted to produce a cryogenic effect at the distal tip thereof. Thus, the insulating sheath 4 is now disposed in surrounding engagement with cryosurgical probe 6.

FIGS. 2–5 of the drawings show the conventional cryosurgical probe 6 of FIG. 1 with the cryogenic distal tip thereof either fully exposed, partially exposed or completely surrounded by an insulating sheath so as to be compatible with conventional cryosurgical methods to freeze and kill the cancerous tissue cells of a patient undergoing treatment. In this regard, either argon gas or liquid nitrogen can be supplied to the distal tip of the cryoprobe 6 to form an ice ball and produce a cryogenic effect which is known to kill cancer cells. For purposes of example only, the cryosurgical probe 6 may be coupled to an argon gas based cryosurgical system such as that manufactured by EndoCare, Inc. of Irvine, Calif. Similar changes in the dimensions of the ice ball can also be achieved by using a liquid nitrogen-based cryosurgical system such as that manufactured by Cryomedical Sciences, Inc.

Figure 2:
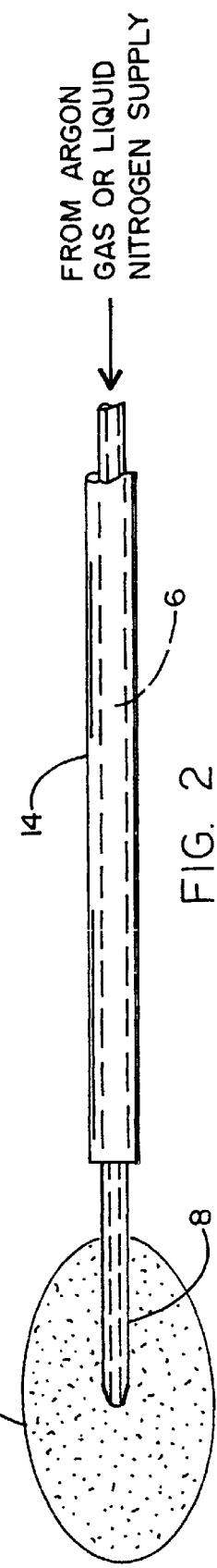

In actual cryosurgery during which the apparatus and method of this invention were tested, it was found that the cryosurgical probe 6 being surrounded by a 1.0 mm thick insulating sheath 14 and having a fully exposed (i.e. unsheathed) distal tip 8 as shown in FIG. 2 of the drawings could be used to form a generally egg shaped ice ball 10 that is suitable to treat a prostate gland having a length of greater than 3.5 cm. In this case, the size and shape of the ice ball 10 were not effected by the sheath 14 with the result that ice balls of greater than 3.5 cm in length were produced.

Where the length of the prostate gland is between 3.0 and 3.5 cm, an insulating sheath 12 having a variable thickness in the manner shown by FIG. 3 of the drawings was employed to surround the cryoprobe 6. More particularly, the thickness of sheath 12 was 2.0 mm for substantially its entire length. This thickness tapered down to a region 13 consisting of the last 0.5 cm of the sheath 12 where the thickness was reduced to 1.0 mm. Either a single sheath having a variable wall thickness along its length or a pair of inner and outer sheaths displaced axially relative to one another can be used. In the case of FIG. 3, the final 1.0 cm of the distal tip 8 of cryoprobe 6 was left exposed and unsheathed. Accordingly, an ice ball 14 was produced having a length of about 3.0 cm.

For a prostate gland having a length of less than 3.0 cm, the cryosurgical probe 6 was surrounded by the insulating sheath 16 of FIG. 4 of the drawings. The sheath 16 had a uniform thickness of 2.0 mm along its entire length. However, the final 1.0 cm of the distal tip 8 of probe 6 was once again left exposed and unsheathed. In this case, a generally spherical ice ball 18 was produced having a diameter of 3.0 cm or less.

For seminal vesicle cryosurgery, the cryosurgical probe 6 was surrounded by the insulating sheath 20 shown in FIG. 5 of the drawings. As in FIG. 4, the sheath 20 has a uniform thickness of 2.0 mm. However, in this case, the sheath 20 covers the entire length of the probe 6 such that no portion of the distal tip 8 is left exposed and unsheathed. The surrounding relationship of cryosurgical probe 6 by insulating sheath 20 as shown in FIG. 5 was found to produce a relatively thin cylindrical ice ball 22 which is ideally suited for matching the shape of the seminal vesicle.

It may now be appreciated that a variety of different sheaths having different wall thickness and length would be available. The precise size, shape and thermal mapping of the different insulating sheaths with different cryosurgical systems can be experimentally determined. However, it would be desirable for the thicker-walled sheaths to have tapered distal tips so as to allow for an easier penetration through the patient's tissue.

As will be known to those experienced in cryosurgical procedures, because of the thermal conductivity of a conventional all metal cryoprobe, freezing is known to occur along areas of the probe which are not actively cryogenic (i.e. are spaced axially from the ice ball formation). During prostate cryosurgery, for example, the probe shaft will sometimes freeze to the tissue of the patient undergoing treatment. In most cases, the patient's tissue will recover from the freezing. However, in some cases a larger than required volume of tissue along the tract of the cryoprobe may freeze. Consequently, a potentially damaging fistula may be formed as a result of freezing more than the targeted tissue area, such as in the brain. Similarly, if the surface of the liver is frozen, it may crack and hemorrhage during thawing which can be life threatening, particularly to those patients with liver cirrhosis. In this same regard, for breast lesions which usually lie close to the surface, freezing large areas of the breast tissue may result in undesirable scarring.

While the thermally insulating sheaths that have been disclosed above when referring to FIGS. 2–5 of the drawings reduce ice formation along the shaft of the cryosurgical probe 6, it was noticed during actual cryosurgery testing that if the insulating sheaths were thin, they were sometimes covered with ice. This effect may not be totally acceptable for cryosurgery involving certain organ systems (e.g. the breast, brain and liver) for the reasons just indicated.

The foregoing problem of freezing the cryoprobe and the thermal insulating sheath thereover may be solved by surrounding the cryoprobe with a heated sheath such as that shown in FIG. 6 of the drawings. In this case, a conventional cryosurgical probe 30 is surrounded by a suitable biocompatible sheath 32 that is manufactured from plastic, foil or the like. The probe 30 and sheath 32 can be inserted and positioned adjacent the targeted tissue area of the patient by the same method that was described above when referring to FIG. 1. The heated sheath 32 is electrically connected to a source of power so that the distal end of the cryosurgical probe 30 will be heated. Therefore, only about the last four centimeters of the sheath 32 needs to be heated. However, the precise length of the sheath 32 as well as the heated area thereof are determined by the type and location of the tissue to be treated. Moreover, only the non-heated portion of the sheath (designed 32-1 in FIG. 5) will be peel-away.

Heat is preferably applied to the sheath 30 by means of a heating grid 34. The heating grid 34 may include electrically conducting wires or thin plates that are preferably embedded in and around the sheath material during manufacture. Power is supplied to the heating grid 34 of sheath 30 via a first electrical wire set 36. The wire set 36 is connected to a control stand 50 at which a source of electric power is available. The control stand 50 has the usual controls 52 by which to regulate the electrical current being supplied to the heating grid 34 of heated sheath 30.

So that the amount of heat generated by the heated sheath 32 can be monitored, a temperature sensor 38 is either mounted outside the heated area of the sheath 32 (as shown) or embedded in the sheath material during manufacture. One or more temperature sensors (only a single sensor 38 being shown for convenience) are located at or along the distal end of the cryosurgical probe 30 and connected to the control stand 50 via a second electrical wire set 38.

The control stand 50 includes a suitable display 54 by which to provide to the health care professional an indication of the heat being generated by heating grid 34 and detected by temperature sensor 38. In this way, freezing along the cryosurgical probe 30 can be prevented while the amount of heat generated can be carefully and accurately controlled to achieve a specific ice ball size and shape according to the size and location of the targeted tissue.

It will be apparent that while a preferred embodiment of the invention has been shown and described, various modifications and changes may be made without departing from the true spirit and scope of the invention. In this regard, it may be appreciated that the length (if any) of the distal tip of the cryosurgical probe of FIGS. 2–5 that is left uncovered (i.e. unsheathed) in combination with the dimensions (e.g. uniform or variable wall thickness) of the insulating sheath or the temperature to which the sheath is heated around the cryosurgical probe of FIG. 6 determine the size and shape of the lethal zone at which the ice ball is effective. To enable the surgeon to accurately measure at the surface level of the skin how to position the insulating sheath relative to the distal end of the cryoprobe, markings (e.g. circumferential rings) can be applied to the sheaths at 0.5 cm intervals, starting about 3.0 cm from each end thereof. To confirm the location of the insulating sheath, conventional ultrasound techniques may be employed.

Having thus set for the preferred embodiment.
What is claimed is:

1. A method for cryosurgically treating the cancerous tissue of a patient by forming an ice ball in proximity to the cancerous tissue to kill the cancer cells, said method comprising the steps of:

forming an access channel through the body of the patient to communicate with the cancerous tissue to be treated;

inserting a cryosurgical probe through the access channel, said cryosurgical probe having a hollow interior, an exterior, and proximal and distal ends;

supplying a cryogen through the hollow interior of said cryosurgical probe to form an ice ball at the distal end thereof; and surrounding at least some of said cryosurgical probe with a thermal insulator that is manufactured from a biocompatible plastic material for controllably adjusting the size and shape of the ice ball to correspond with the size, shape and location of the cancerous tissue and positioning said thermal insulator to extend around the exterior of said cryosurgical probe so as to prevent a direct contact of said probe with the tissue of the patient and reduce freezing of said cryosurgical probe where said probe is surrounded by said thermal insulator.

2. The method recited in claim 1, comprising the additional steps of forming the access channel through the patient's body by inserting a hollow dilator surrounded by said thermal insulator, removing said hollow dilator from the patient's body after the access channel has been formed while leaving said thermal insulator in place, and sliding said cryosurgical probe through the access channel so that said probe is surrounded by said thermal insulator.

3. The method recited in claim 1, wherein said thermal insulator has a variable thickness along the length thereof.

4. The method recited in claim 3, comprising the additional step of positioning the distal end of said cryosurgical probe outwardly from said thermal insulator so that said distal end is exposed relative to said thermal insulator.

5. The method recited in claim 1, comprising the additional step of surrounding the distal end of said cryosurgical probe with said thermal insulator.

6. The method recited in claim 1, comprising the additional step of heating the thermal insulator so as to enable the size and shape of the ice ball to be controllably adjusted depending upon the temperature to which the thermal insulator is heated.

7. In a cryosurgical probe for cryosurgically treating the cancerous tissue of a patient, said cryosurgical probe having proximal and distal ends and adapted to receive a cryogen by which to form an ice ball at said distal end in proximity to the cancerous tissue to be treated so as to kill the cancer cells, the improvement comprising:

a thermal insulator surrounding at least some of said cryosurgical probe to controllably adjust the size and shape of the ice ball to correspond with the size, shape and location of the cancerous tissue; and a heating element embedded within said thermal insulator to heat said thermal insulator so that the size and shape of the ice ball can be controllably adjusted depending upon the temperature to which said thermal insulator is heated.

8. The improvement recited in claim 7, wherein said thermal insulator is manufactured from a biocompatible plastic material.

9. The improvement recited in claim 7, wherein said thermal insulator has a variable thickness along the length thereof.

10. The improvement recited in claim 7, wherein said thermal insulator surrounds the distal end of said cryosurgical probe.

11. The improvement recited in claim 7, wherein the distal end of said cryosurgical probe is disposed outwardly from and exposed relative to said thermal insulator.

12. The improvement recited in claim 7, further comprising a temperature sensor coupled to said thermal insulator to monitor the temperature to which said thermal insulator is heated.

13. A method for cryosurgically treating the cancerous tissue of a patient by forming an ice ball in proximity to the cancerous tissue to kill the cancer cells, said method comprising the steps of:

surrounding a tissue dilator with a removable thermal insulator and inserting said tissue dilator through the tissue of the patient to form an access channel that communicates with the cancerous tissue to be treated;

removing said tissue dilator from the patient's body after said access channel has been formed while leaving said thermal insulator in place within said access channel;

sliding a cryosurgical probe through said access channel so that said probe is surrounded by said thermal insulator, said cryosurgical probe having proximal and distal ends; and supplying a cryogen through said cryosurgical probe to form an ice ball at the distal end thereof, said thermal insulator controlling the size and shape of the ice ball to correspond with the size, shape and location of the cancerous tissue to be treated.

14. The method recited in claim 13, wherein said thermal insulator is manufactured from a biocompatible plastic material.

15. The method recited in claim 13, wherein said thermal insulator has a variable thickness along the length thereof.

16. The method recited in claim 13, comprising the additional step of positioning the distal end of said cryosurgical probe outwardly from said thermal insulator so that said distal end is exposed relative to said thermal insulator.

17. The method recited in claim 13, comprising the additional step of surrounding the distal end of said cryosurgical probe with said thermal insulator.

18. The method recited in claim 13, comprising the additional step of heating the thermal insulator so as to enable the size and shape of the ice ball to be controllably adjusted depending upon the temperature to which the thermal insulator is heated.

19. The method recited in claim 18, comprising the additional step of heating said thermal insulator by means of a heating element embedded therewithin.

20. The method recited in claim 18, including the additional step of coupling a temperature sensor to said thermal insulator to monitor the temperature to which said thermal insulator is heated.

* * * * *